(12) United States Patent
Du Plessis et al.

(10) Patent No.: US 8,395,226 B2
(45) Date of Patent: Mar. 12, 2013

(54) MICROCHIP-BASED MOEMS AND WAVEGUIDE DEVICE

(75) Inventors: Monuko Du Plessis, Pretoria (ZA); Lukas Willem Snyman, Pretoria (ZA)

(73) Assignee: Insiava (Pty) Limited, Pretoria (ZA)

( * ) Notice: Subject to any disclaimer, the term of this patent is extended or adjusted under 35 U.S.C. 154(b) by 0 days.

(21) Appl. No.: 13/146,469

(22) PCT Filed: Jan. 27, 2010
(Under 37 CFR 1.47)

(86) PCT No.: PCT/IB2010/050356
§ 371 (c)(1),
(2), (4) Date: Mar. 19, 2012

(87) PCT Pub. No.: WO2010/086798
PCT Pub. Date: Aug. 5, 2010

(65) Prior Publication Data
US 2012/0175642 A1    Jul. 12, 2012

(30) Foreign Application Priority Data
Jan. 27, 2009  (ZA) .................... 2009/00632

(51) Int. Cl.
*H01L 29/84*    (2006.01)

(52) U.S. Cl. ........ 257/415; 257/414; 257/417; 257/432; 257/428; 438/48; 438/50; 438/54; 385/14

(58) Field of Classification Search .............. 257/84, 257/98, 414–417, 431, 432, 428; 438/7, 438/16, 31, 32, 48, 50, 54; 385/14
See application file for complete search history.

(56) References Cited

U.S. PATENT DOCUMENTS

| | | | | |
|---|---|---|---|---|
| 6,636,653 | B2 * | 10/2003 | Miracky et al. | 385/14 |
| 2003/0202730 | A1 * | 10/2003 | Fujieda et al. | 385/14 |
| 2009/0289266 | A1 * | 11/2009 | Lee et al. | 257/84 |

FOREIGN PATENT DOCUMENTS

| | | |
|---|---|---|
| DE | 103 42 331 | 5/2005 |
| EP | 0 398 085 | 11/1990 |
| EP | 1 748 290 | 1/2007 |
| WO | WO 99/04234 | 1/1999 |

OTHER PUBLICATIONS

International Search Report for PCT/IB2010/050356, mailed Apr. 6, 2010.
International Preliminary Report on Patentability for PCT/IB2010/050356, with four (4) Amended Sheets, mailed Apr. 18, 2011.

* cited by examiner

*Primary Examiner* — Tammy Pham
*Assistant Examiner* — Jay C Chang
(74) *Attorney, Agent, or Firm* — Nixon & Vanderhye PC

(57) ABSTRACT

An electro-optical device 10 comprises a body 12 of a semiconductor material, such as silicon. A light source 14 is formed integrally in the body. The device comprises an associated light detector 16 and an optical path providing part 19 having a refractive index and extending between the light source 14 and the detector 16, to provide an optical path 18 having a path length. A sensor 20 cooperates with the optical path providing part 19 and is configured to modulate light emitted by the light source 14, by changing at least one of light absorption characteristics in the optical path by exposing a medium in the optical path to the emitted light, the path length and the refractive index.

16 Claims, 7 Drawing Sheets

MICROCHIP-BASED MOEMS AND WAVEGUIDE DEVICE

This application is the U.S. national phase, under 35 U.S.C. §371, of International Application No. PCT/IB2010/050356, filed 27 Jan. 2010, which claims priority to South Africa Application No. 2009/00632, filed 27 Jan. 2009, the entire contents of each of which are hereby incorporated herein by reference.

INTRODUCTION AND BACKGROUND

This invention relates to electro-optical devices, more specifically micro optical-electrical-mechanical (MOEMS) devices.

MOEMS devices for measuring physical parameters such as temperature, mechanical shock, motion, acceleration, rotation, light levels, fluid flow rate, counting of particles in a flow system, fluorescence and absorption of such particles are known. However, the known devices are sophisticated and/or complex and/or costly.

OBJECT OF THE INVENTION

Accordingly, it is an object of the present invention to provide an electro-optical device with which the applicant believes the aforementioned problems and/or disadvantages may at least be alleviated or which may provide a useful alternative for the known devices.

SUMMARY OF THE INVENTION

According to the invention there is provided an electro-optical device comprising:
 a body of a semiconductor material;
 a light source formed integrally in the body for emitting light;
 an associated light detector;
 an optical path providing part having a refractive index and extending between the light source and the associated detector to provide an optical path having a path length; and
 a sensor cooperating with the optical path providing part and being configured to modulate the emitted light by changing at least one of light absorption characteristics in the optical path by exposing a medium in the optical path to the emitted light, the path length and the refractive index.

The medium may be a fluid in the form of a gas or liquid, or may be in the solid state.

The associated detector may be a discrete device. In other embodiments, the detector may be integrally formed in the body.

The optical path providing part may comprise a waveguide. The sensor may at least partially be provided by the waveguide.

The optical path may have a first end and a second end, the light source may be in light communication relationship with the first end, the associated detector may be in light communication relationship with the second end and the sensor may be provided intermediate the first end and the second end.

In other embodiments, the optical path may have a first end and a second end and the light source and associated detector may be in light communication relationship with the first end.

At least part of the sensor may be provided adjacent the second end.

The sensor may comprise a mechanical component which may at least partially be located in the optical path. The component may comprise a cantilever.

The sensor may comprise a cavity in the optical path and which cavity is configured for admitting the medium into the optical path, so that the emitted light is transmitted through the medium before it reaches the detector, or is reflected by the medium, before it reaches the detector.

The cavity may be provided by a microfluidic device.

At least part of the sensor may be integrally formed in the body.

The device may comprise signal and/or data processing circuitry integrated in the body of semiconductor material and connected to at least one of the light source and the associated detector.

The light source may comprise a first pn junction and the device may comprise a terminal arrangement configured to reverse bias the first pn junction into a breakdown mode, to emit light. The source may also comprise a second pn junction and the terminal arrangement may be configured to forward bias the second pn junction, to inject carriers into the first pn junction.

The semiconductor material may comprise a direct bandgap semiconductor material.

In other embodiments, the semiconductor material may comprise an indirect bandgap semiconductor material. The indirect bandgap semiconductor material may comprise silicon. At least the light source and associated detector may be integrally formed in the body of silicon by a CMOS technology.

BRIEF DESCRIPTION OF THE ACCOMPANYING DIAGRAMS

The invention will now further be described, by way of example only, with reference to the accompanying diagrams wherein.

DESCRIPTION OF A PREFERRED EMBODIMENT OF THE INVENTION

Figure 1:
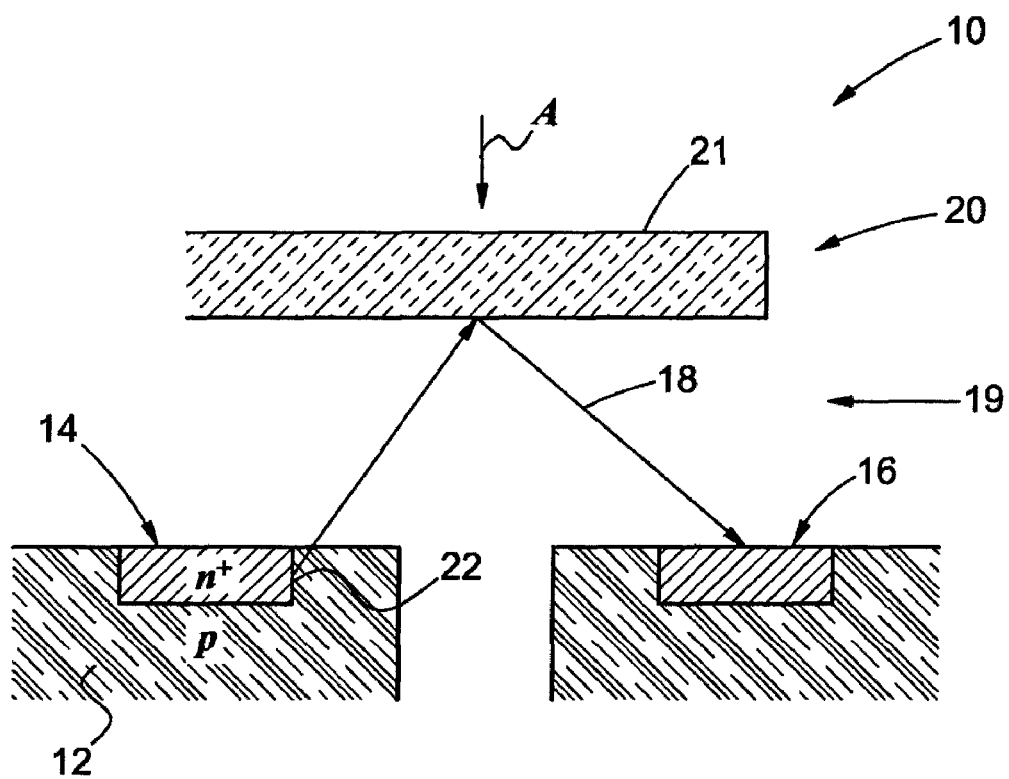
FIG. 1 is a high level diagram of a first example embodiment of an electro-optical device according to the invention.

An electro-optical device according to the invention is generally designated by the reference numeral 10 in FIG. 1.

The electro-optical device 10 comprises a body 12 of a semiconductor material. A light source 14 is formed integrally in the body. The device comprises an associated light detector 16 and an optical path providing part 19 having a refractive index and extending between the light source 14 and the associated detector 16 to provide an optical path 18 having a path length. The device further comprises a sensor 20 cooperating with the optical path providing part 19 and being configured to modulate light emitted by the light source 14 and before the light is detected by the detector 16 by changing at least one of light absorption characteristics in the optical path by exposing a medium in the optical path to the emitted light, the path length and the refractive index. The medium may be a fluid in the form of a gas or liquid, or may be in the solid state.

Stationary and surface mounted light source 14 emits light. The light is guided through a first section of optical path 18 to the sensor 20 comprising the cantilever or arm 21 from where it is reflected and guided through a second section of the optical path 18 and detected by the detector 16. Due to an external perturbation A to be sensed or measured, the arm 21 is caused to move relative to the stationary light source 14. This causes a change in the path length of the optical path 18, which modulates the light emitted by the light source and which modulation is detected in the form of a phase or intensity change in the signal detected by the detector.

The semiconductor material may be a direct bandgap material. Alternatively, the material is an indirect bandgap material, such as Si, Ge and Si—Ge. The light source 14 comprises at least a first pn junction 22 and the device 10 comprises a terminal arrangement (not shown) configured to reverse bias the first pn junction 22 into a breakdown mode, to emit light. The breakdown mode may be one of an avalanche breakdown mode, field emission breakdown mode and a combination of avalanche breakdown and field emission breakdown.

If an infrared optical source is chosen, waveguides providing or defining at least part of the optical path 18 should be of SiON and the detector 16 should be of Si—Ge type. If Si LEDS's operating in the region of 1100 nm or higher are selected, Si—Ge or other suitable detectors should be used. If short submicron wavelength integrated Si LED's are utilized, the waveguides may be of suitable low loss, of glassy type, and standard Si PIN detector arrangements may be utilized.

In other embodiments, the waveguide 19 may be of Si and the light source 14 may comprise a light emitting Si—Ge heterojunction device.

Figure 2:
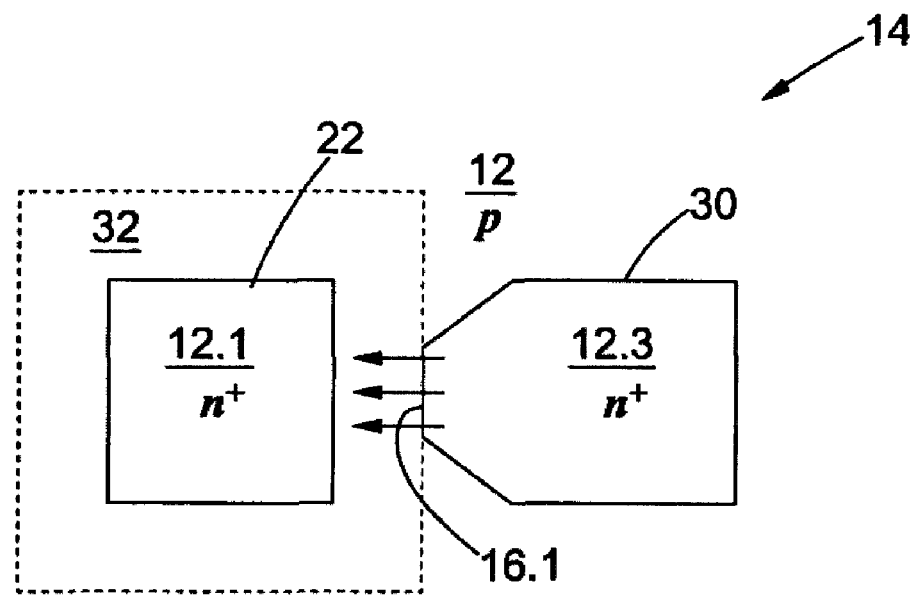
FIG. 2 is a basic diagram illustrating one example embodiment of an integrated optical source of the device.

For example and referring to FIG. 2, the optical source 14 may comprise a second pn junction 30 and the terminal arrangement is configured to forward bias the second pn junction 30, to inject carriers into the first pn junction 22. More particularly, the optical source 14 may be configured such that a first depletion region 32 associated with the first junction 22 punches through to a second depletion region associated with at least part of the second junction 30, thereby to lower an energy barrier of the at least part of the second junction 30.

Figure 3:
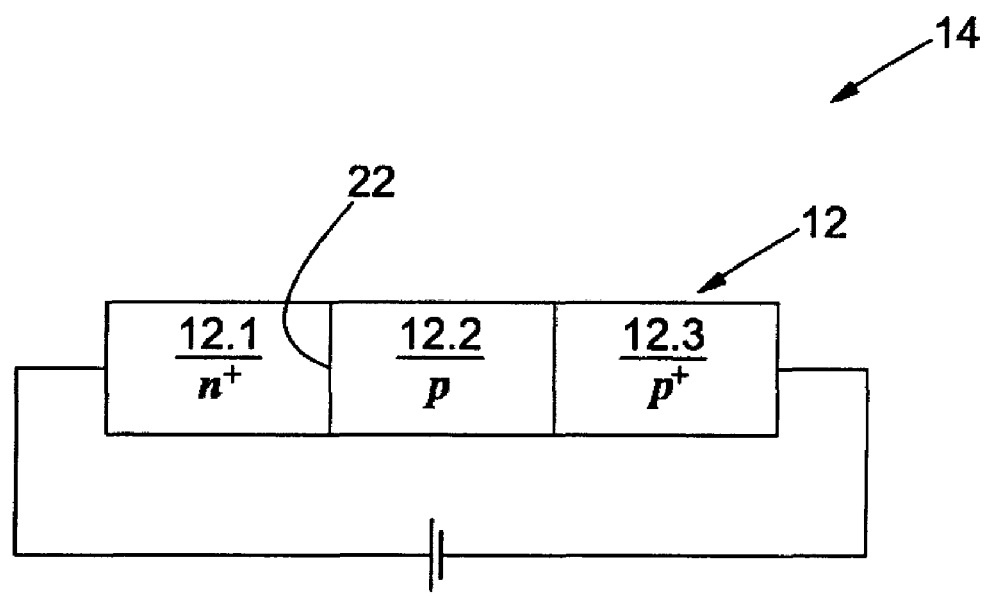
FIG. 3 is a similar diagram illustrating another example embodiment of the integrated optical source of the device.

Further for example and referring to FIG. 3, the first junction 22 may be formed between a first region 12.1 of the body 12 of a first doping kind of a first concentration and a second region 12.2 of the body of a second doping kind of a second concentration. A third region 12.3 of the body of the second doping kind and of a third concentration, which is higher than the second concentration, is provided on another side of the second region as the first region, so that the second region is sandwiched between the first region and the third region. The source 14 is configured such that a first depletion region associated with the first junction 22 reaches through the second region 12.2 to reach the third region 12.3, before the first junction 22 enters the breakdown mode.

The radiation wavelength of these devices 14 ranges from the ultraviolet region, through the visible region, to the infrared region. Through filtering techniques, selected particular bandwidth regions and magnitudes may be selected.

These devices can be integrated into CMOS integrated circuitry with no or little change in design and processing procedures. Should higher intensity and narrower bandwidth be required, other diodes or laser diodes could also be used.

Figure 4:
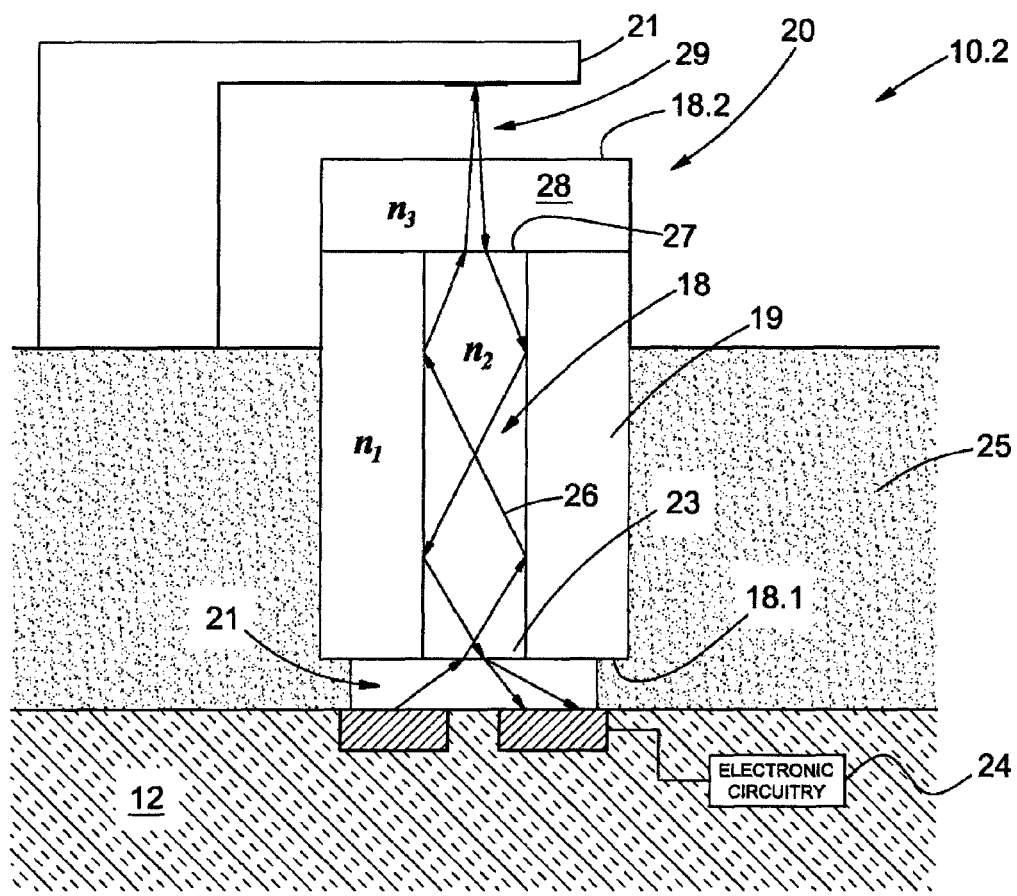
FIG. 4 is a high level diagram of a second example embodiment of the device.

In FIG. 4, there is shown another hybrid embodiment of the device designated 10.2. The stationary light source 14 and detector 16 are integrally formed in the silicon body. The optical path 18 is defined by a waveguide 19 which is surface mounted on the body and recessed in overlaying layers 25 of the chip body 12. The optical path has a first end 18.1 which is in light communication relationship with both the light source 14 and the detector 16 and a second end 18.2. The sensor 20 comprising a a mechanical component such as cantilever 21 is mounted adjacent the second end 18.2, but spaced therefrom, to define a cavity 29 for admitting a medium into the optical path. Also integrated in the silicon body 12 is electronic circuitry 24 which may be connected to the light source 14 and/or the detector 16. The circuitry 24 may comprise biasing circuitry, control circuitry and/or signal processing circuitry and/or data processing circuitry.

The hybrid device 10.2 comprises three separate modules or bodies, viz a semiconductor chip body 12 with integrated optical source 14 and associated detector 16, an optical path providing part 19 defining optical path 18 and a sensor 20 for interfacing with the environment and parameters to be sensed or measured. The stationary optical source 14 emits an optical signal of a narrow bandwidth into a recess or cavity 21, formed in the CMOS over layers 25. The emitted optical signal impacts on a partially reflecting surface 23. A first part of the emitted signal is reflected to the integrated detector 16. A second part of the signal is refracted into optical path 18 and follows internal reflection paths 26. At a second partially reflecting surface 27, a first part of the second part of the signal is reflected back towards the body 12. This first part of the second part of the signal interferes with the aforementioned first part of the signal and causes intensity or phase change in the signal reaching the detector 16. A second part of the second part of the signal enters a n3 refraction index region 28 of the waveguide 19, and propagates substantially normally to this region, then propagates through the second cavity 29 and is reflected back at a reflecting surface on arm 21. A part of this signal returns back into the optical path 18 and contributes to phase contrast and intensity change at the detector 16.

Hence, the sensor 20 comprising at least one of waveguide 19, arm 21 and cavity 29 impose phase changes and/or intensity changes at the detector 16. Both these changes are a function of or dependent on the physical status or perturbations of the sensor. For example, if the temperature of the waveguide 19 changes, the total path length of the signal in the optical path changes and will cause a detectable change at the detector 16. Also, should the position of arm 21 relative to stationary source 14 change, the path length changes and causes a detectable phase or intensity change at the detector 16. Shock, motion, acceleration or rotation of the device may all impose position changes of the reflecting surface on arm 21 and result in changes detectable by the detector 16.

Ambient light levels may be detected in the cavity 29 (normally occupied by air) by providing a progressive stepping increase in the intensity of the signal emitted by the source 14 and monitoring when suitable phase contrast changes are detected according to predetermined levels when the intensity of the signal is higher than that of ambient light.

The cavity 29 may also be utilized to monitor status or parameter changes in this cavity e.g., if a fluid flow is introduced through the cavity 29. The arm 21 may be appropriately modified to facilitate detection of a fluid flow rate. If particles of a high optical absorption flow through cavity 29, this is expected to impose sharp changes in the intensity of the signal transmitted through cavity 29 and received at the detector and which may enable particle counts by the processing circuitry 24. Similarly, other properties such as absorption and fluorescence as caused by the particles may impose changes on the intensity as detected by the detector 16.

The device 10 may be adapted to optimize same for a particular physical parameter measurement. For greater sensitivity in motion and movement parameters, the arm 21 and cavity 29 may be tailor-designed, to optimize this measurement.

Figure 5:
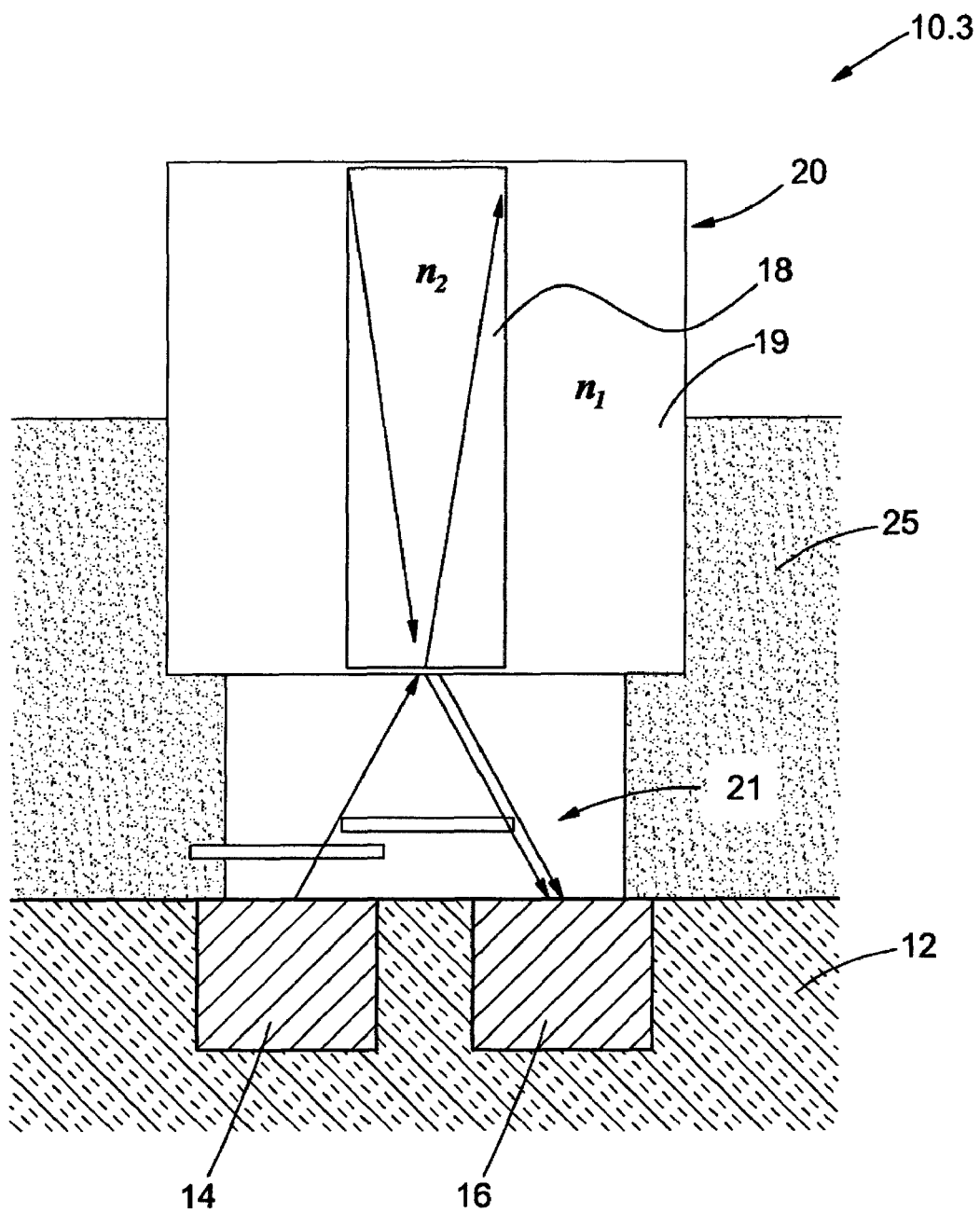
FIG. 5 is a high level diagram of a third example embodiment of the device.

For temperature sensitivity, the arm 21 may be omitted and the waveguide 19 defining the optical path part 18 of the device may have a suitable length in order to detect temperature changes. Such an embodiment is shown at 10.3 in FIG. 5.

Figure 6:
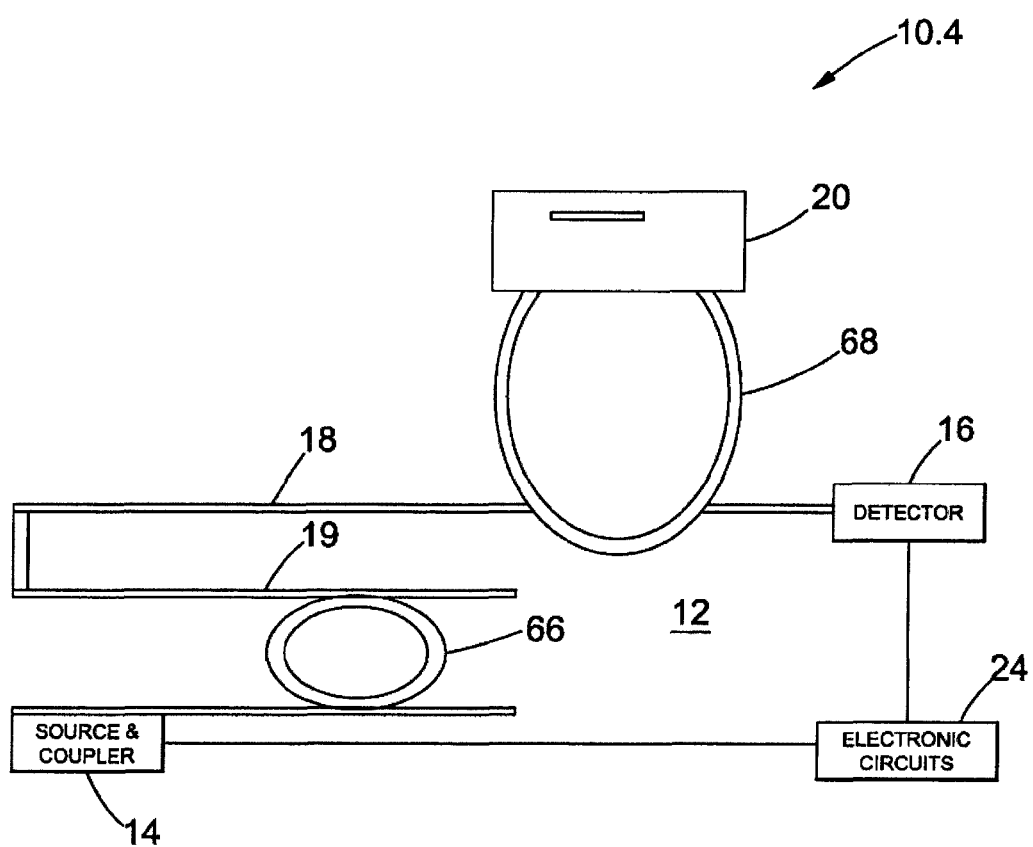
FIG. 6 is a high level diagram of a fourth example embodiment of the device.

In FIG. 6 there is shown an embodiment 10.4 of the device wherein the entire device is integrated in one silicon body 12 with standard CMOS fabrication techniques and provided in one package. It is believed that such embodiments would offer considerable advantages with regard to new innovative applications in the electronic systems world, reduction in manufacturing cost, miniaturization of systems, etc. The onboard integration of the optical source 14, the associated detector 16, the waveguide 19 for the optical path 18 as well as the sensor 20 offers diverse advantages with retrieving optical signals and processing and changes in the detected optical signals with adjacently lying CMOS electronics and signal processing circuitry 24. Several further specialized components such as omni-directional emitters, optical filters, optical splitters, optical interferometers, Mach Zender unbalanced phase contrast detectors, as well as mechanical, optical absorption, and chemical sensing areas may be added to the device in order to increase its integratabilty and/or efficiency. The device 10.4 shown in FIG. 6 also comprises a ring resonator 66 for dropping an optical signal with a selected wavelength into the waveguide 19 and an unbalanced Mach Zender arrangement 68 with one extended arm. This arm can be designed to interface with sensor 20 comprising optical arms or actuators, as described herein. The reflected light returned to the Mach Zender arrangement 68 is filtered and the introduced phase and intensity changes detected at detector 16.

Hence, a fully integrated MOEMS system 10.4 is provided on one CMOS chip in monolithic form, using both bulk and surface machining techniques to manufacture optical waveguide 19 and mechanical sensing and actuating structures 20 on a CMOS chip 12, which already contains the light source 14, optical detector 16 and necessary electronic circuits 24. The light source and optical detector are an integral part of the CMOS integrated circuit, intimately integrated with all the necessary electronic biasing, sensing and signal processing circuitry 24 onto a CMOS chip 12.

To this end the necessary electronic circuits 24 and optoelectronic devices 14, 16 and 19 are manufactured in a state-of-the-art CMOS process. The electronic circuits may include all biasing networks, signal processing circuits, readout circuits, etc. Hence, the optoelectronic components integrated with the CMOS circuitry includes the light source 14, optical detector 16 and waveguides 19 defining at least part of the optical path 18, using standard CMOS layers, etc.

By utilising both surface machining and bulk machining MEMS technology techniques, additional structures can be added onto or into the silicon CMOS chip. This processing can be done after completion of the CMOS process (post processing), during CMOS processing or before the CMOS process starts (pre-processing).

Additional structures added to the CMOS chip may include optoelectronic and micro-optics components, for example optical modulators, waveguides, resonators, filters, reflectors, etc. The sensor 20 or mechanical components may include any one or more of cantilevers, membranes, microfluidic devices, micropumps, cavities, trenches, etc. The optical, mechanical and electronic integration makes MOEMS (micro-optical electromechanical systems) feasible on a single chip.

Using the fully integrated CMOS and MEMS based structures, sensor and actuator systems can be manufactured onto one semiconductor chip, not using a hybrid approach where some form of chip-to-chip bonding is used.

These sensing and actuating, optical, mechanical and electronic systems can be combined in several applications. Certain layers added onto the CMOS chip using surface machining techniques can also act as chemical or biological sensing structures, to further broaden the application of MOEMS systems on chip.

Further applications of the device 10, 10.2, 10.3 and 10.4 include interfacing of the device with other systems realized on board of the CMOS chip such as an optical link module that may used for optically pulsing other sections or circuitry on the chip. In other applications, the device may indeed be used to generate such optical clock and optical transmission pulses on the CMOS chip, being transmitted over large areas of the chip body 12 and interfacing with a large number of chip subsections (not shown).

The sensor 20 may comprise a mere cavity for admitting a fluid into the optical path part.

Temperature, physical movement, absorption of light and other physical parameters to be sensed or measured, through sensor 20, induce intensity and/or phase changes at the detector 16. Similarly, a medium moving through the cavity 29 and optical path 18 will induce intensity changes at the detector 16. By applying appropriate electronic signal processing in the processing section 24 on the microchip, the device can detect a whole range of physical parameters such as temperature changes, motion, shock, vibration, acceleration, rotation, light levels, fluid flow, particle and absorption counts, and fluorescent characteristics of objects introduced in the cavity 29.

Figure 7:
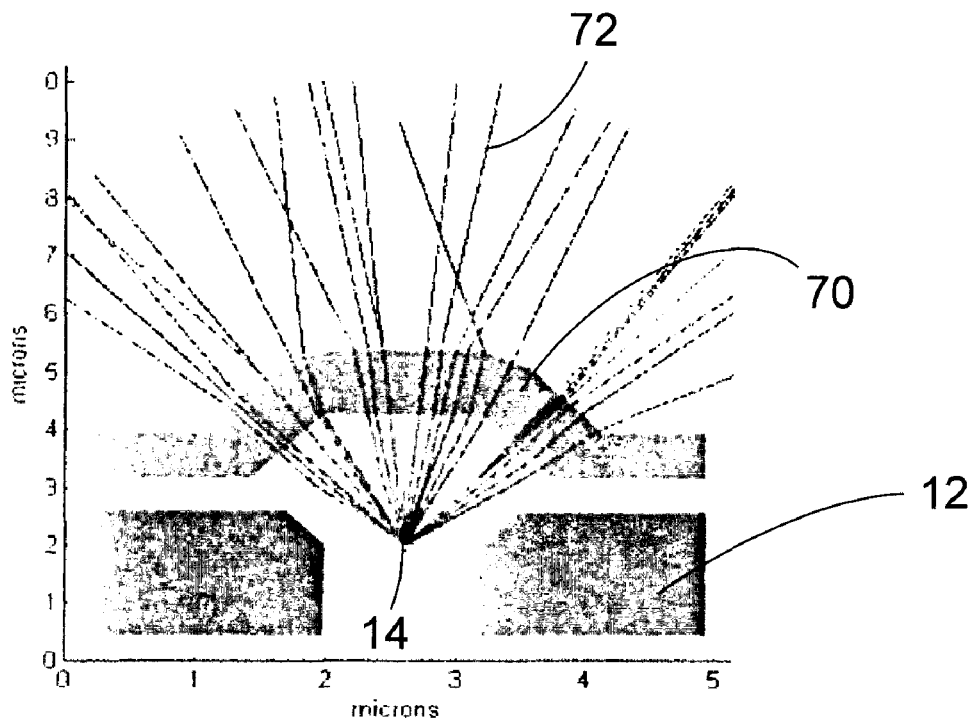
FIGS. 7 to 10 are similar diagrams illustrating various example optical emission and/or coupling mechanisms for use in the device according to the invention.

The realization of the devices 10, 10.2, 10.3 and 10.4 may require dedicated directional emitters, electro-optical coupling structures as well as waveguiding technology in CMOS integrated circuitry, utilizing CMOS design and processing procedures, as far as possible. Examples of such structures are illustrated in FIGS. 7 to 10. In these structures the refraction characteristics of various over-layers as encountered in CMOS integrated circuit technology, the geometric definition of these layers in terms of curvature and surface bending as well as placement of micro-dimensioned Si LED optical sources 14 have mainly been used to achieve these goals. All these changes may be implemented where necessary, by slightly changing the CMOS design and processing procedures in localized regions on the chip 12. In FIG. 7 semi-omni-directional emission by SI-LED 14 is achieved by mainly utilizing the curvature possibilities of oxide passivation and silicon nitride passivation layers 70, in order to maximize the optical emission 72 through the surface layers to the environment.

Figure 8:
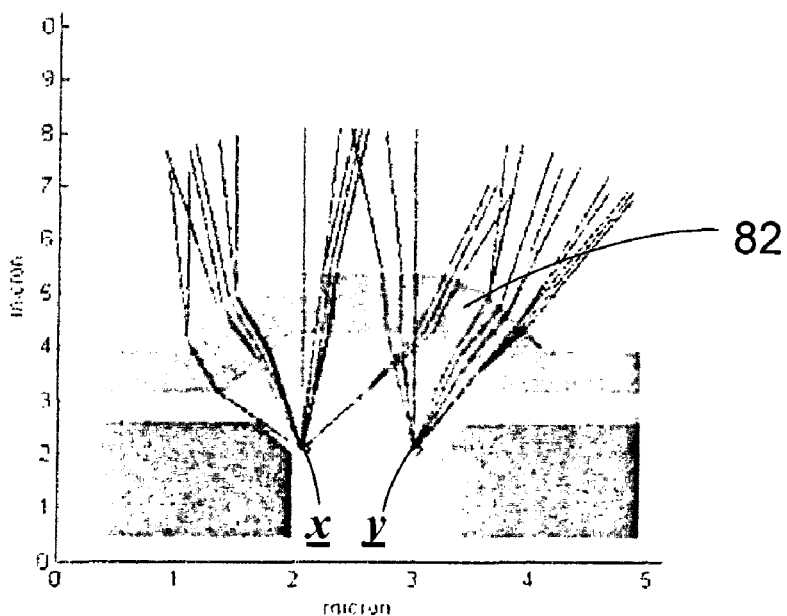

FIG. 8 illustrates the same basic spherical silicon nitride structure 82 as in FIG. 7, but the source position has been shifted. When the source is placed at position X, a clear focusing of almost all rays emitting vertically from the structure is observed. When the source is placed at position Y, a clear directional emission of the radiation towards a slanted 45 degree angle is observed, also with some focusing or converging of optical rays present.

Figure 9:
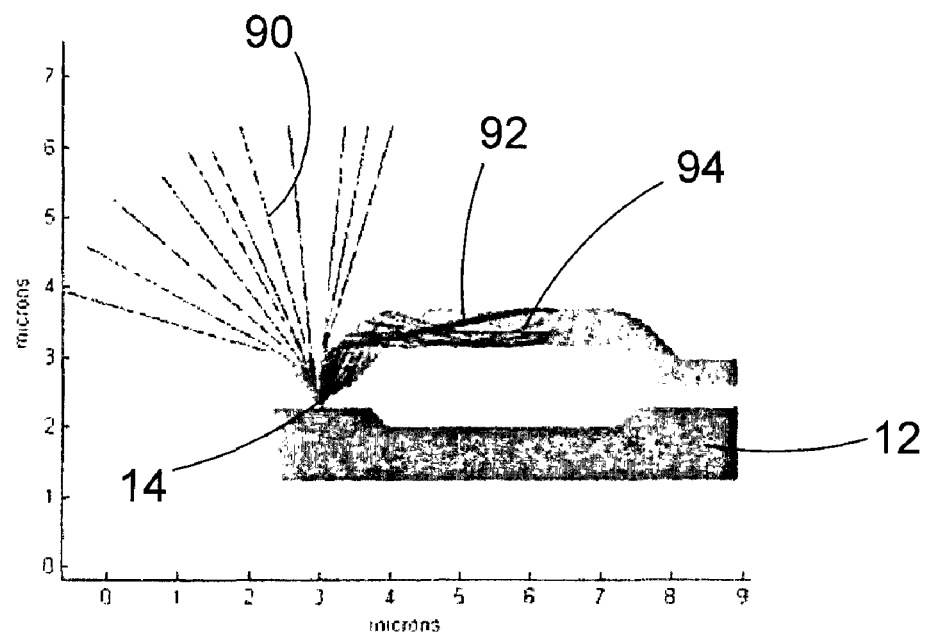

FIG. 9 illustrates a structure that could be used to create optical splitting of the optically radiated power in more or less equal parts and in two different paths. In this case, a 0.3 micron field oxide layer and 1 micron silicon passivation and plasma deposited layers were assumed as commonly encountered in 0.35 micron CMOS technology. One part 90 of the radiation propagates out of the structure into air, and the other part 92 propagates laterally into a silicon nitride layer 94. Optical splitters of this kind may have wide and diverse applications in MOEMS applications and can be used to generate interference and phase contrast in certain applications.

Figure 10:
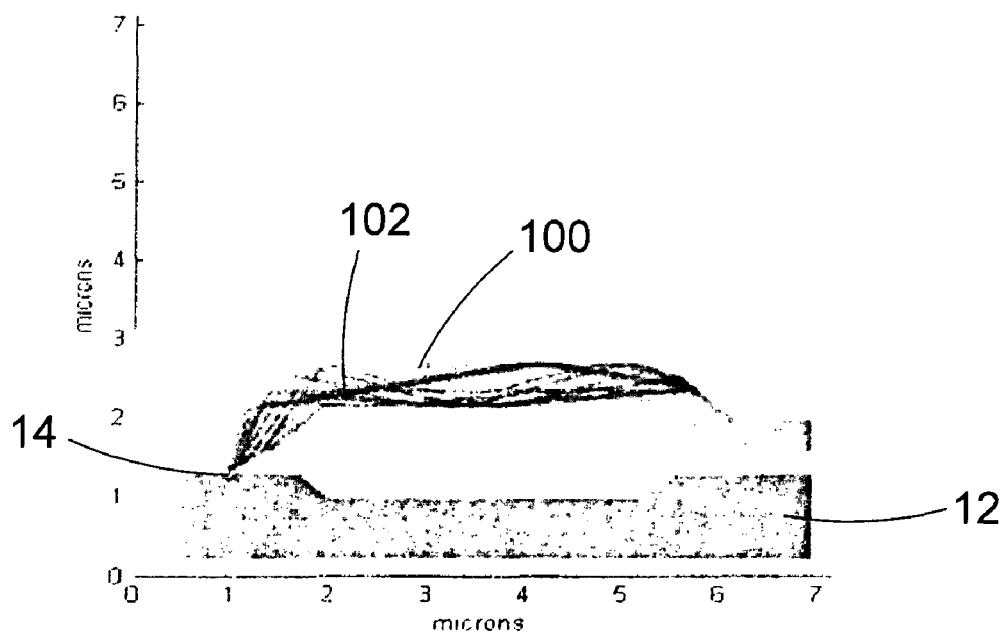

FIG. 10 illustrates optimized lateral wave-guiding longitudinally along the silicon nitride layer 100 for a very high proportion of the totally emitted Si LED radiation 102. The plasma oxide layer thickness has been reduced locally and the optical emission point in the generated structure was positioned near the "bird peak" point in the silicon oxide layer. Initial analysis shows that launch angles ranging from 34°-76° couple effectively into the silicon nitride layer 100. Due to the lower refractive indexes of both the plasma and field oxide below the layer and the refractive index of air above the layer, initial indications are that the radiation can be quite effectively guided along the silicon nitride layer 100. The silicon nitride is effectively transparent for the longer wavelengths above 600 nm. Special layers utilizing silicon oxinitride ($SiO_xN_x$) compositions offer transparency at lower wavelengths. In both cases the waveguided or transmitted radiation are still much lower than the absorption edge wavelength for Si detectors (approximately 950 nm). The combination of Si LED light source, optical waveguiding or optical transmission, together with good Si detectors that can be incorporated into the silicon CMOS structure makes diverse optical processing and MOEMS applications and realizations a viable option. The current total optical emission levels as can be extracted from Si CMOS LEDs are of the order of 1-100 nW in micron area dimensions (with compatible CMOS operating voltages and currents). These emission levels are much higher than the low frequency detectivity level for Si pn detectors of comparable dimensions (with typical floor levels of pW). This leaves nearly a three order range in the power link budget, which can accommodate various losses and splitting of optical radiation. The power link budget even allows for various cavity resonant structures to be fabricated in silicon CMOS structures that may even allow lasing or improved phase contrast characteristics of the emitted radiation.

The integrated silicon light sources 14 herein described have a wide bandwidth of about 350 nm to about 950 nm, even 1100 nm, and the device 10 may therefore be used in spectral analyses of light reflected by or transmitted through a medium located in or guided through the optical path 18, by utilizing a linear detector or other detector 16 configured to detect spectral content.

The device 10, 10.2 10.3 and 10.4 may be suitably hermetically sealed (not shown) and further tailor-designed in order to avoid all other imposing or unwanted noise or perturbing signals for the particular purpose.

The invention claimed is:

1. An electro-optical device comprising:
   a first body of a semiconductor material;
   a light source comprising a first pn junction formed integrally in the first body;
   a terminal arrangement configured to reverse bias the first pn junction into a breakdown mode for emitting light;
   an associated light detector formed in a second body of the semiconductor material;
   an optical path providing part having a refractive index and extending between the light source and the associated detector to provide an optical path having a path length; and
   a sensor cooperating with the optical path providing part and being configured to modulate the emitted light by changing at least one of: the path length, the refractive index and light absorption characteristics in the optical path by exposing a medium in the optical path to the emitted light,
   wherein the second body and the first body are the same so that the associated detector is integrally formed in the first body.

2. A device as claimed in claim 1 wherein the optical path providing part comprises a waveguide.

3. A device as claimed in claim 2 wherein the sensor is at least partially provided by the waveguide.

4. A device as claimed in claim 1 wherein the optical path has a first end and a second end, wherein the light source is in light communication relationship with the first end, wherein the associated detector is in light communication relationship with the second end and wherein the sensor is provided intermediate the first end and the second end.

5. A device as claimed in claim 1 wherein the optical path has a first end and a second end, wherein the light source and associated detector are in light communication relationship with the first end.

6. A device as claimed in claim 5 wherein at least part of the sensor is provided adjacent the second end.

7. A device as claimed in claim 1 wherein the sensor comprises a mechanical component which is at least partially located in the optical path.

8. A device as claimed in claim 7 wherein the mechanical component comprises a cantilever.

9. A device as claimed in claim 1 wherein the sensor comprises a cavity in the optical path and which cavity is configured for admitting the medium into the optical path.

10. A device as claimed in claim 9 wherein the cavity is provided by a microfluidic device.

11. A device as claimed in claim 1 wherein at least part of the sensor is integrally formed in the body.

12. A device as claimed in claim 1 comprising signal and/or data processing circuitry integrated in the body of semiconductor material and connected to at least one of the light source and the associated detector.

13. A device as claimed in any one of claim 12 wherein the light source comprises a second pn junction and wherein the terminal arrangement is configured to forward bias the second pn junction, to inject carriers into the first pn junction.

14. A device as claimed in claim 1 the semiconductor material comprises an indirect bandgap semiconductor material.

15. A device as claimed in claim 14 wherein the indirect bandgap semiconductor material comprises silicon.

16. A device as claimed in claim 15 wherein at least the light source and associated detector are integrally formed in the body of silicon by a CMOS technology.

* * * * *